(12) United States Patent
Souza

(10) Patent No.: US 10,265,396 B2
(45) Date of Patent: Apr. 23, 2019

(54) MAGNETIC EXTRACELLULAR MATRIX

(71) Applicant: NANO3D BIOSCIENCES INC, Houston, TX (US)

(72) Inventor: Glauco R. Souza, Houston, TX (US)

(73) Assignee: Greiner Bio-One North America, Inc., Monroe, NC (US)

( * ) Notice: Subject to any disclaimer, the term of this patent is extended or adjusted under 35 U.S.C. 154(b) by 0 days.

(21) Appl. No.: 15/708,089

(22) Filed: Sep. 18, 2017

(65) Prior Publication Data

US 2018/0000936 A1 Jan. 4, 2018

Related U.S. Application Data

(62) Division of application No. 14/404,469, filed as application No. PCT/US2013/045246 on Jun. 11, 2013, now Pat. No. 9,764,030.

(60) Provisional application No. 61/659,970, filed on Jun. 14, 2012.

(51) Int. Cl.
| | | |
|---|---|---|
| *A61K 41/00* | (2006.01) | |
| *A61N 2/00* | (2006.01) | |
| *C12N 5/00* | (2006.01) | |
| *A61L 27/18* | (2006.01) | |
| *A61L 27/38* | (2006.01) | |
| *A61L 27/50* | (2006.01) | |
| *G01N 33/543* | (2006.01) | |
| *G01N 33/58* | (2006.01) | |
| *B03C 1/01* | (2006.01) | |
| *B03C 1/034* | (2006.01) | |
| *B03C 1/30* | (2006.01) | |

(52) U.S. Cl.
CPC .......... *A61K 41/0052* (2013.01); *A61L 27/18* (2013.01); *A61L 27/38* (2013.01); *A61L 27/50* (2013.01); *A61N 2/00* (2013.01); *C12N 5/0062* (2013.01); *C12N 5/0068* (2013.01); *G01N 33/54346* (2013.01); *G01N 33/587* (2013.01); *A61L 2400/12* (2013.01); *A61L 2430/20* (2013.01); *A61L 2430/30* (2013.01); *B03C 1/01* (2013.01); *B03C 1/034* (2013.01); *B03C 1/30* (2013.01); *B03C 2201/26* (2013.01); *C12N 2529/00* (2013.01)

(58) Field of Classification Search
None
See application file for complete search history.

(56) References Cited

U.S. PATENT DOCUMENTS 7,326,571 B2 * 2/2008 Freyman ................ A61K 35/28
424/400

OTHER PUBLICATIONS

Derfus, Austin M., et al. "Remotely triggered release from magnetic nanoparticles." Advanced materials 19.22 (2007): 3932-3936 (Year: 2007).*
Kibbey, Maura C. "Maintenance of the EHS sarcoma and Matrigel preparation." Journal of tissue culture methods 16.3-4 (1994): 227-230. (Year: 1994).*

* cited by examiner

*Primary Examiner* — Robert J Yamasaki
(74) *Attorney, Agent, or Firm* — Boulware & Valoir

(57) ABSTRACT

Methods of making and using a magnetic ECM are disclosed. The ECM comprises positively and negatively charged nanoparticles, wherein one of said nanoparticles contains a magnetically responsive element. When the magnetic ECM is seeded with cells, the cells will be magnetized and can be levitated for 3-D cell culture.

10 Claims, 2 Drawing Sheets

MAGNETIC EXTRACELLULAR MATRIX

PRIOR RELATED APPLICATIONS

This application claims priority to 61/659,970, filed Jun. 14, 2012, PCT/US2013/045246, filed Jun. 11, 2013, and Ser. No. 14/404,469, filed Nov. 27, 2014, each of which is incorporated by reference in its entirety herein for all purposes.

FEDERALLY SPONSORED RESEARCH STATEMENT

Not applicable.

FIELD OF THE INVENTION

The invention relates to materials, methods of making, and methods of using a magnetic extracellular matrix.

BACKGROUND OF THE INVENTION

The extracellular matrix or "ECM" is the extracellular part of animal tissue. Due to its diverse nature and composition, the ECM can serve many functions. Functions include providing support, segregating tissues from one another, regulating intercellular communication, and the cell's dynamic behavior. To make matters even more complex, the structure and composition of the ECM are constantly changing in response to the current metabolic activity of the resident cell population, the mechanical demands of the tissue, and the prevailing microenvironmental niche conditions. This concept of "dynamic reciprocity" between the ECM and the resident cell population is a major advantage for the use of ECM scaffold materials over synthetic materials and emphasizes the importance of maintaining as much of both the native composition and its ultrastructure as possible during the preparation of three-dimensional scaffolds.

Components of the ECM are produced intracellularly by resident cells, and secreted (and/or accumulated) into the ECM via exocytosis or cell death. Once secreted they then aggregate with the existing matrix. The ECM is composed of an interlocking mesh of glycosaminoglycans (GAGs) and fibrous proteins, which are discussed below.

GAGs are carbohydrate polymers and are usually attached to extracellular matrix proteins to form proteoglycans (hyaluronic acid is a notable exception, see below). Proteoglycans have a net negative charge that attracts positively charged sodium ions (Na+) which attracts water molecules via osmosis, keeping the ECM and resident cells hydrated. Proteoglycans may also help to trap and store growth factors within the ECM.

Different types of proteoglycan found within the extracellular matrix. Heparan sulfate (HS) is a linear polysaccharide found in all animal tissues. It occurs as a proteoglycan (PG) in which two or three HS chains are attached in close proximity to cell surface or extracellular matrix proteins. It is in this form that HS binds to a variety of protein ligands and regulates a wide variety of biological activities, including developmental processes, angiogenesis, blood coagulation and tumour metastasis.

In the extracellular matrix, especially basement membranes, the multi-domain proteins perlecan, agrin and collagen XVIII are the main proteins to which heparan sulfate is attached.

Chondroitin sulfates contribute to the tensile strength of cartilage, tendons, ligaments and walls of the aorta. They have also been known to affect neuroplasticity.

Keratan sulfates have a variable sulfate content and unlike many other GAGs, do not contain uronic acid. They are present in the cornea, cartilage, bones and the horns of animals.

Hyaluronic acid (or "hyaluronan") is a polysaccharide consisting of alternative residues of D-glucuronic acid and N-acetylglucosamine, and unlike other GAGs it is not found as a proteoglycan. Hyaluronic acid in the extracellular space confers upon tissues the ability to resist compression by providing a counteracting turgor (swelling) force by absorbing significant amounts of water. Hyaluronic acid is thus found in abundance in the ECM of load-bearing joints. It is also a chief component of the interstitial gel. Hyaluronic acid is found on the inner surface of the cell membrane and is translocated out of the cell during biosynthesis. It acts as an environmental cue that regulates cell behavior during embryonic development, healing processes, inflammation and tumor development, and interacts with a specific transmembrane receptor, CD44.

Collagens are the most abundant protein in the ECM in most animals. In fact, collagen is the most abundant protein in the human body and accounts for 90% of bone matrix protein content. Collagens are present in the ECM as fibrillar proteins and give structural support to resident cells. Collagen is exocytosed in precursor form (procollagen), which is then cleaved by procollagen proteases to allow extracellular assembly.

The collagen can be divided into several families according to the types of structure they form:
Fibrillar (Type I,II,III,V,XI)
Facit (Type IX,XII,XIV)
Short chain (Type VIII,X)
Basement membrane (Type IV)
Other (Type VI,VII,XIII)

Elastins, in contrast to collagens, give elasticity to tissues, allowing them to stretch when needed and then return to their original state. This is useful in blood vessels, the lungs, in skin, and the ligamentum nuchae, and such tissues contain high amounts of elastins. Elastins are synthesized by fibroblasts and smooth muscle cells. They are very insoluble, and tropoelastins are secreted inside a chaperone molecule, which releases the precursor molecule upon contact with a fiber of mature elastin. Tropoelastins are then deaminated to become incorporated into the elastin strand.

Fibronectins are glycoproteins that connect cells with collagen fibers in the ECM, allowing cells to move through the ECM. Fibronectins bind collagen and cell surface integrins, causing a reorganization of the cell's cytoskeleton and facilitating cell movement. Fibronectins are secreted by cells in an unfolded, inactive form. Binding to integrins unfolds fibronectin molecules, allowing them to form dimers so that they can function properly. Fibronectins also help at the site of tissue injury by binding to platelets during blood clotting and facilitating cell movement to the affected area during wound healing.

Laminins are proteins found in the basal laminae of virtually all animals. Rather than forming collagen-like fibers, laminins form networks of web-like structures that resist tensile forces in the basal lamina. They also assist in cell adhesion. Laminins bind other ECM components such as collagens, nidogens, and entactins.

Many cells bind to components of the extracellular matrix. Cell adhesion can occur in two ways; by focal adhesions, connecting the ECM to actin filaments of the cell, and hemidesmosomes, connecting the ECM to intermediate filaments such as keratin. This cell-to-ECM adhesion is regulated by specific cell surface cellular adhesion molecules (CAM) known as integrins. Integrins are cell surface proteins that bind cells to ECM structures, such as fibronectin and laminin, and also to integrin proteins on the surface of other cells.

Fibronectins bind to ECM macromolecules and facilitate their binding to transmembrane integrins. The attachment of fibronectin to the extracellular domain initiates intracellular signaling pathways as well as association with the cellular cytoskeleton via a set of adaptor molecules such as actin.

There are many cell types that contribute to the development of the various types of extracellular matrix found in plethora of tissue types. However, fibroblasts are the most common cell type in connective tissue ECM, in which they synthesize, maintain and provide a structural framework. Fibroblasts also secrete the precursor components of the ECM, including the ground substance. Other cell types include stem cells, as well as chondrocytes and osteoblasts, amoung others. Chondrocytes are found in cartilage and produce the cartilagenous matrix. Osteoblasts are responsible for bone formation.

The ECM is of intense medical and scientific interest because it can be used to provide a scaffold for tissue growth and regeneration. Because native ECM guides organ development, repair and physiologic regeneration, it provides a promising alternative to synthetic scaffolds and a foundation for regenerative efforts.

In the last few years, studies have confirmed the importance of ECM in regualting stem cells differentiation in mature tissue. Many of the factors responsible for the influence of ECM on stem cells are related to its properties, including matrix structure, composition, elasticity, and integrity. Because these ECM properties are often tissue type specific, in order for developing differentiated cells from stem cells for therapeutic applications, the capability of generating specific ECM types may be of great value to regulate stem cell environments (Reilly, 2010).

One of the recent paradigm shifts in stem cell biology has been the discovery that stem cells can begin to differentiate into mature tissue cells when exposed to intrinsic properties of the extracellular matrix (ECM), such as matrix structure, elasticity, and composition. These parameters are known to modulate the forces a cell can exert upon its matrix. Mechano-sensitive pathways subsequently convert these biophysical cues into biochemical signals that commit the cell to a specific lineage. Just as with well-studied growth factors, ECM parameters are extremely dynamic and are spatially- and temporally-controlled during development, suggesting that they play a morphogenetic role in guiding differentiation and arrangement of cells. Our ability to dynamically regulate the stem cell niche the way it naturally occurs in the body is likely to be a critical requirement for developing differentiated cells from stem cells for therapeutic applications.

ECM has been prepared by harvesting an appropriate tissue and decellularizing it with chemical and/or enzymatic means of cell lysis, and/or physical means of stripping cells, such as forced flow over or through the tissue. However, these methods require a lot of time, provide low yields, and usually a patient cannot provide such tissue, necessitating resource to cadavers or animal tissues. Thus, the existing methodology is not ideal.

Another method of preparing ECM is to make it from cells grown in culture. Cells gown in monolayer have been used to make ECM, but the technique is difficult and subject to very low yields. Further, 2D cultures do not fully and accurately reflect the organization and structure of native ECM, again making such methods less than ideal.

Although some of these approaches are promising, there is still room for improved methods of preparing and using ECM that avoids some of the disadvantages of the prior art and provides high yield ECM that is as close to native ECM as possible.

SUMMARY OF THE INVENTION

Herein, we present new biomimetic, three-dimensional scaffolds that can be used therapeutically to treat disease. The invention takes advantage of the 3D culture method developed by Nano3D BioSciences™ Inc, and uses those methods to grow 3D cultures, from which a magnetic ECM can be prepared.

In patent application WO2010036957 by Nano3D Biosciences®, cells are levitated in a magnetic field by contacting the cells with a "hydrogel" comprising a bacteriophage with nanoparticles that are responsive to a magnetic field. In particular, filamentous phage, such as fd, fl, or M13 bacteriophage, are used. How the method works is not completely clear, but it is theorized that the phage provide a gel-like structure or assembly that coats the cells, and somehow assists the cells to uptake or adsorb the magnetically responsive nanoparticles. Thus, even when the hydrogel is washed away, the cells remains magnetically responsive, and can be levitated in an appropriate magnetic field.

Although the hydrogel is mostly washed away, the potential for phage infectivity or transfer of genetic material remains, and thus it was desired to provide a material that allows cell uptake or adsorption without the use of phage. WO2011038370, also by Nano3D Biosciences®, thus describes a second generation nanoparticle assembly, which completely avoids the use of bacteriophage to enable the magnetization of cells. Furthermore, a variation of the claimed nanoparticle assembly is now commercially available at Nano3D Biosciences® (Houston Tex.), under the trade name NANOSHUTTLE.™ This new magnetic material provides a superior method of magnetizing cells without the use of any toxic or infectious agents, and the cells remain magnetized when the material is washed away.

It has now been discovered that the NANOSHUTTLE™ technology can be used to prepare magnetic ECM, and magnetic levitation used as a tool to aid in the decellularization and handling of the ECM. This novel discovery is the basis for the various inventions described herein.

Generally speaking, the method includes growing cells in 3D culture using a magnetic nanoparticles. The magnetic nanoparticles are taken up by the cells, but eventually end up in the ECM, such that the ECM can be magnetically levitated and/or separated from the multicellular structure. The ECM can thus be held in place using a magnet, and the 3D culture decellularized, using any known methodology, to produce a cell free, magnetic ECM that can then be used for any of the variety of uses that ECM can be employed for.

The general steps include:

1. Treating of cells, mixtures of cells, or tissue fragments with NANOSHUTTLE™ or any another magnetic nanoparticle solution, such that the cells uptake magnetic nanoparticles.

2. 3D cell culture is performed to enable cells to generate ECM resulting from 3D multicellular structure formation. Preferably magnetic levitation of the cells or mixtures of cells is performed because of its capability to rapidly generate 3D multicellular structures, and growth of such 3D cultures until a desired size is reached. As long as cells uptake magnetic nanoparticles, other 3D culturing methods can be used in this step, such as rotating reactors, scaffolds, hanging drop, non-adhering surfaces, round-bottom flasks, or any 3D cell culturing bio-reactor.

3. Decellularization of the 3D culture using any chemical, enzymatic and/or physical methods.

4. Recovery of the now decellularized magnetic ECM by magnetic separation of magnetic ECM from debris, or any other recovery method.

5. Removal of surfactant or other chemicals by washing the magnetically held ECM, or any other wash method.

6. Steps 1-5 can be repeated as many times as needed if enriching or increasing the amount of ECM accumulated on the mangnetic nanoparticle ECM is desirable or needed. This is accomplished by retreating fresh cells or tissue in step 1 with the magnetizes ECM product resulting from step 5.

7. Reseeding the ECM and further use as desired.

The invention includes any one or more of the following embodiments, in all possible combinations:

- A magnetic ECM or seeded magnetic CM made by any method herein described.
- A method of making a magnetic ECM, said method comprising: placing magnetic nanoparticles inside a cell; levitating said cell in a magnetic field and growing said levitated cell in said magnetic field into a 3D cell culture; and decellularizing said 3D cell culture to produce a magnetic ECM.
- A method of making a magnetic ECM, said method comprising: mixing cells with a composition comprising a magnetically responsive nanoparticle such that the cells uptake said magnetically responsive nanoparticle; levitating said magnetic cells in a magnetic field; growing said levitated cells in said magnetic field into a 3D cell culture; and decellularizing said 3D cell culture to produce a magnetic ECM.
- A method of making a magnetic ECM, said method comprising: mixing cells with a composition comprising: a negatively charged nanoparticle; a positively charged nanoparticle; and a support molecule; wherein one of said negatively charged nanoparticle or positively charged nanoparticle contains a magnetically responsive element, and wherein said support molecule holds said negatively charged nanoparticle and said positively charged nanoparticle in an intimate admixture; levitating said cells in a magnetic field and growing said levitated cells in said magnetic field into a 3D cell culture; and decellularizing said 3D cell culture to produce a magnetic ECM.
- A method of preparing tissue for implantation in a patient, said method comprising: combining cells with magnetic nanoparticles that are taken up by said cells; exposing said cells to a magnetic field such that said cells coalesce and levitate; growing said cells to form a 3D cell culture; decellularizing said 3D cell culture to make a magnetic ECM; seeding said magnetic ECM with allogeneic stem or progenitor cells from a patient; growing said seeded ECM in a magnetic field; and transplanting the seeded ECM into said patient. If desired, the original cells can also be from the patient, but this is not essential, as the ECM is nearly completely decellularized.

Other embodiments include, seeding said magnetic ECM with cells, and growing said seeded ECM in a magnetic field; seeding said magnetic ECM with fibroblast cells, and stem or progenitor cells, and further growing said seeded ECM in a magnetic field; seeding said magnetic ECM with epithelial cells and stem or progenitor cells, and further growing said seeded ECM in a magnetic field; seeding said magnetic ECM with osteoblast cells and stem or progenitor cells, and further growing said seeded ECM in a magnetic field; seeding said magnetic ECM with autologous fibroblast cells, epithelial cells and stem or progenitor cells from a patient, and further growing said seeded ECM in a magnetic field; or seeding said ECM with stem or progenitor cells from said patient, and further growing said seeded ECM in a magnetic field, and variations and combinations thereof.

In preferred embodiments, the original cells and/or reseeding cells can be from any suitable source, e.g., are from cells lines or allogenic cells, or combinations thereof. Preferably, allogenic cells from a younger patient are preferred, as stem cells are known to be more easily amplified using ECM prepared from younger animals. The cells can originate in the form of a tissue fragment, or in the form of a tissue fragment extracted from a patient.

The types and numbers of cells necessary for recellularization varies significantly with the organ as well as with the size and complexity of the ECM, tissue fragments being simpler than whole orgrans. Preferably, the cells types selected are such as would be required in the issue of interest, eg., ostoblasts for bone tissue, etc. The parenchymal cells, the cell types responsible for the specific functions of the organ, are of obvious necessity, e.g., hepatocytes in liver, cardiomyocytes in heart, epithelium in lung, etc. In addition, nonparenchymal cells such as fibroblasts and endothelial cells enhance the functional phenotype of the parenchymal cells and contribute to the organization of the cellular architecture of the tissue. Endothelial cells are important to provide a nonthrombotic barrier for the decellularized organ matrix and assure that blood flow in vivo is confined to the vascular spaces and the parenchymal cells are protected from the shear stress created by the flow. The fibroblast, which secretes and remodels the ECM, is clearly important and they improve parenchymal cell functions in co-cultures. Recently, it was shown that fibroblasts are also involved in the electrical properties of the myocardium by coupling with the cardiomyocytes and aiding in the propagation of the electrical stimuli over longer distances.

Depending on the organ, other cell types can also be important, if not necessary, for functional recellularization. To date, the increased complexity of dealing with multiple cell types has limited co-culture studies mostly to the use of endothelial cells and fibroblasts. Dealing with a mixture of cells is a combinatorial problem, and as in the case of tissue-engineered bladders, serendipity or extensive testing may be necessary to find the optimal seeding and culture protocol.

The cells can be levitated with any magnetic nanoparticle that can be taken up by the cell or otherwise introduced into the cell, e.g., by blasting, injection, electroporation, transduction, cationic liposomes, hydrogels, magnetic pressure, and the like. It is anticipated that any means of introduction will suffice, although active uptake means, such as described below, may be the least cell perturbing method, and thus be preferred.

In preferred embodiments, the cells are levitated with a composition comprising: a) a negatively charged nanoparticle; b) a positively charged nanoparticle; and c) a support molecule, wherein one of said negatively charged nanoparticle or positively charged nanoparticle contains a magnetically responsive material, such as iron or iron oxide, and wherein said support molecule holds said negatively charged nanoparticle and said positively charged nanoparticle in an intimate admixture.

Most preferred, the composition is NANOSHUTTLE™, which is known to work and which is commercially available from Nano3D BioSciences (Houston Tex.).

Further, as described in prior patents, variously shaped 3D cultures can be made by modifying the shape of the magnetic field. For example, a ring magnet can be used to make a ring or donut shaped 3D culture. Magnetic fields can also be used to maintain or change such shape during the decellularization and recellularization processes.

The ECM can the be prepared from the 3D culture by any method known in the art, including but not limited to treatment with surfactants, non-ionic detergents, ionic detergents, zwitterionic detergents, alkaline treatment, acid treatment, proteases, nucleases, endonucleases, exonucleases, osmotic pressure, hypertonic solutions, hypotonic solutions, freeze-thaw, perfusion, sonication, agitation, and combinations of the above. The 3D culture can be minced or otherwise sliced, diced or fragmented before treatment, or the 3D culture decellularized intact.

The magnetic ECM can be used in any of the methods for which ECM is used, but has particular application when reseeded and grown in magnetically levitated 3D culture. For example, the ECM can be seeded with stem cells from a patient, as well other cell types appropriate for the application, and the resulting 3D culture used in various cell or tissue therapies.

Further, the magnetic ECM can be used in the study of ECM components and/or the differentiation of cell types, and to that end any of the components of the ECM (or cells) can be labelled, e.g., with antibodies, GFP, fluorescent labels, and the like.

The following abbreviations may be used herein:

| Abbreviation | Definition |
| --- | --- |
| BAP | Bone alkaline phosphatase |
| BrEpic | Bronchial Epithelial |
| CHAPS | 3-[(3-cholamidopropyl)dimethylammonio]-1-propanesulfonate |
| DAPI | 4',6-diamidino-2-phenylindole-a fluorescent nucleic acid stain. |
| DMEM | Dulbecco's Modified Eagle's Medium |
| ECM | Extracellular matrix |
| EDTA | Ethylenediaminetetraacetic acid |
| FBS | Fetal Bovine Serum |
| HEK | Human Embryonic Kidney |
| HPF | human primary fibroblast |
| mECM | Magnetic ECM |
| mECM-HPF | Magnetic ECM from HPF cells |
| NNDF | human neonatal dermal fibroblasts |
| −NP | negatively charged nanoparticle |
| +NP | positively charged nanoparticle |
| NS | NANOSHUTTLE ™ |
| P/S | Penicillin/Streptomycin |
| PBS | Phosphate buffered saline |
| PL | poly-lysine |
| pNPP | p-Nitrophenyl phosphate |
| RT | Room temperature |
| SDS | Sodium dodecyl suphate |
| SM | support molecule |
| SMC | smooth muscle cells |
| TX100 | Triton-X100 |

By "culturing" herein, we include culturing single cell types or co-culturing more than one cell type.

As used herein a "magnetic ECM" is an extracellular matrix that has been decellularized and contains sufficient magnetic nanoparticles intimately admixed therewith, such that said magnetic ECM will levitate in a magnetic field.

As used herein a "decellularized" means that at least 95% of the cells have been removed, preferably 98%, 99% or more.

As used herein a "positively charged nanoparticle" or "positive nanoparticle" is defined as any particle less than 200 nm, preferably 100 nm or less, that has an over all positive charge. Preferably, the particle is non-toxic, but this is not essential as the particles do not remain with the cells.

As used herein a "negatively charged nanoparticle" or negative nanoparticle" is defined as any particle less than 200 nm, preferably 100 nm, and most preferably about 2-25 nm, that has an over all negative charge. Preferably, the particle is non-toxic, but this is not essential as the particles do not remain with the cells for a long period of time.

As used herein "magnetically responsive element" can be any element or molecule that will respond to a magnetic field. As detailed below, one of the nanoparticles must contain or be a magnetically responsive element.

As used herein "support molecule" refers to any long molecule that will interact with the nanoparticles to create a mat like fibrous structure or gel and thus hold the magnetic nanoparticle in close proximity with the cell for uptake.

By "stem cell" herein, we include toti- and multi-potent cells, unless specifically indicated otherwise.

DESCRIPTION OF EMBODIMENTS OF THE INVENTION

Figure 1:
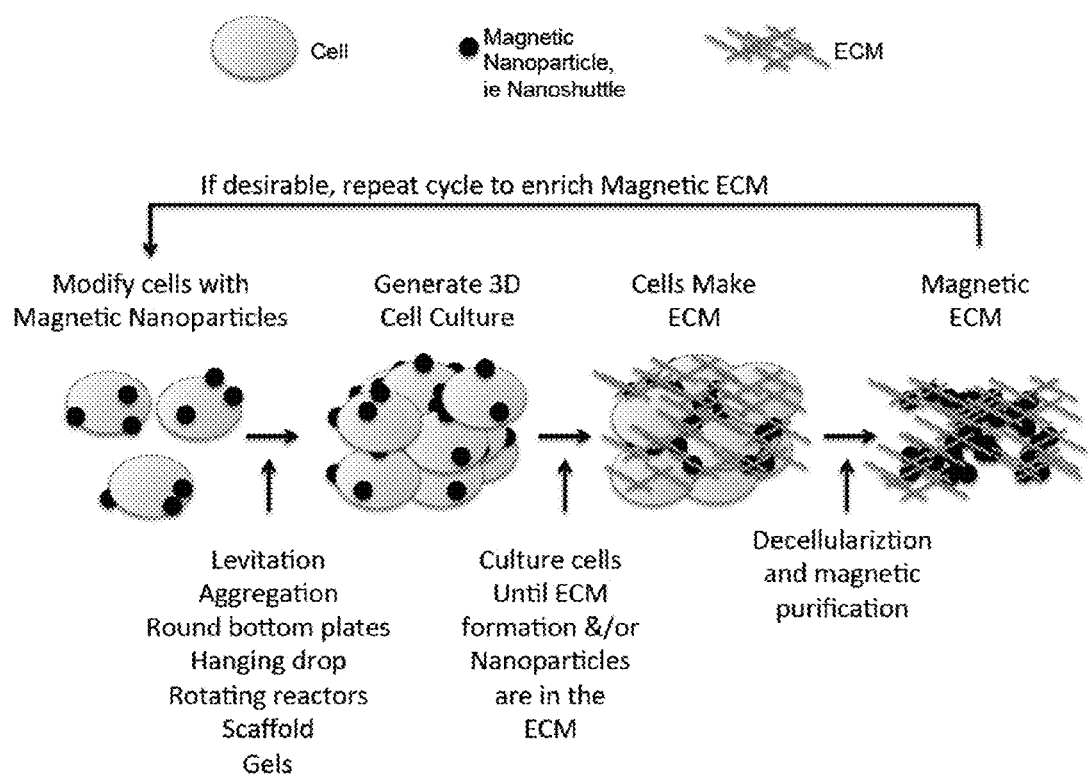
FIG. 1. Schematic of decellularization process using a single cell type.

Generally speaking, the invention is a magnetic ECM, and methods of making and using same. A magnetic material is used that allows cells to uptake or adsorb magnetically responsive elements, and thus be levitable in cell culture when a magnetic field is applied.

In preferred embodiments, the magnetic materials include positively and negatively charged nanoparticles, one of which must contain one or more magnetically responsive elements, such as nanosized iron oxide. These nanoparticles are further combined with a polymer, preferably a cellular polymer, or other long molecule that acts as a support (herein called a "support molecule") for the charged nanoparticles and the cells, holding the nanoparticles in place for their uptake or adsorption by the cells. The inclusion of both positive and negative nanoparticles allows intimate admixing of the nanoparticles and drives the assembly of the three components, thus ensuring even distribution and good uptake. The support molecule intimately combines all three components with the cells in fibrous mat-like structure that allows the cells to take up the magnetically responsive element.

After a period of incubation, the magnetic material can be washed away, allowing the cells to be manipulated in a magnetic field. The magnetic nanoparticles are eventually lost from the cells by 8 days, but we now know they are retained by the ECM, allowing the preparation and use of a magnetic ECM. An intact 3D cell culture can be decellularized by any known method, or minced 3D culture fragments can be decellularized, depending on the ultimate use of the ECM. The magnetic ECM can then be seeded with desired cells, such as autologous stem cells, and cultured in a very natural 3D environment.

The magnetically responsive element can be any element or molecule that will respond to a magnetic field, e.g., rare earth magnets (e.g., samarium cobalt (SmCo) and neodymium iron boron (NdFeB)), ceramic magnet materials (e.g., strontium ferrite), the magnetic elements (e.g., iron, cobalt, and nickel and their alloys and oxides). Particularly preferred are paramagnetic materials that react to a magnetic field, but are not magnets themselves, as this allows for easier assembly of the materials.

Preferably, the magnetic field used to levitate such cells or the magnetic ECM is about 300 G-1000 G. However, the field strength varies with both distance from the culture, and with the amount and type of magnetic response element taken up or adsorbed by the ECM. Thus, the optimal field strength will vary, but is easily determined empirically.

The negatively charged nanoparticles include charge stabilized metals (e.g. silver, copper, platinum, palladium), but preferably is a gold nanoparticle.

The positively charged nanoparticles include surfactant or polymer stabilized or coated alloys and/or oxides (e.g. elementary iron, iron-cobalt, nickel oxide), and preferably is an iron oxide nanoparticle.

One of the two nanoparticles must be magnetically responsive, but obviously either one (or both) could contain this feature.

The nanoparticles should have a nano-scale size, and thus are about 100 nm. Size can range, however, between about 5-250 nm, 50-200 nm, 75-150 nm, but they can be smaller or larger, provided only that the size is appropriate to allow entry or adsorption to the cell type in use. We have shown in other work that there is an upper limit on the effective size of the magnetic nanoparticle, and micrometer size is too big for effectiveness, although some functionality was still observed.

The "support molecule" is generally a polymer or other long molecule that serves to hold the nanoparticles and cells together in an intimate admixture. The support molecule can be positively charged, negatively charged, of mixed charge, or neutral, and can be combinations of more than one support molecule.

Examples of such support molecules include the natural polymers, such as peptides, polysaccharides, nucleic acids, and the like, but synthetic polymers can also be employed. Particularly preferred support molecules include poly-lysine, fibronectin, collagen, laminin, BSA, hyaluronan, glycosaminoglycan, anionic, non-sulfated glycosaminoglycan, gelatin, nucleic acid, extracellular matrix protein mixtures, matrigel, antibodies, and mixtures and derivatives thereof.

Generally speaking, the concentration of the support molecule is substantially greater than the concentration of the negatively and positively charged nanoparticles, ranging from 10-1000 fold greater, 20-500, or 50-200 fold greater. However, greater or lesser amounts are possible, depending on what cell type is being used and which support molecule and nanoparticles are being used. The longer the polymer, the less may be needed to form sufficient structure to hold the nanoparticles in place for uptake.

Generally, the nanoparticles are used in very low concentrations. Concentrations can range between $10^{-12}$-$10^{-6}$ Molar, but are preferably in the nanomolar range, and the support molecule(s) $10^{-9}$-$10^{-3}$ Molar, and are preferably in the micromolar range.

The three components assemble by electrostatic interaction, and thus charged or mixed charge support molecules, such as poly-lysine, are preferred. However, any of the three components can be functionalized, derivatized, or coated so as to further promote interaction of the components and/or the cells. Thus, one or more members can be functionalized, derivatized, or coated with an antibody that e.g., binds to a cell surface antigen. Thus, interactions between the components and/or the cells would be further promoted. Other binding pairs included receptors-ligands, biotin-strepavidin, complementary nucleic acids, wheat germ agglutinin (WGA), sialic acid containing molecules, and the like.

Coatings can also include protective or passivating coatings, particularly for the nanoparticles, such as PVP, dextran, BSA, PEG, and the like. The nanoparticles, especially the nanoparticle that comprises the magnetically responsive element, can be labeled for visualization, e.g., with a fluorophore, radiolabel, or the like, particularly during the development and in vitro testing of magnetized cells and tissues. However, for therapeutic uses, it may be preferred to omit such labels.

In other embodiments, the compositions include the magnetic ECM alone or together with the cells that will be co-cultured therewith, including, but not limited to, stem or progenitor cells, cancer cells, primary cells, mammalian cells, human cells (particularly autologous cells), cells extracted directly from fresh tissue, bacteria, yeast, plant cells, or mixtures thereof.

If desired the magnetic nanoparticle assembly can be made free from biological molecules, such as phage or cell products because the support molecules, such as poly-lysine, can easily be made synthetically. Yet all of the components are generally non-toxic, inexpensive or easy to make. Further, the fibrous mat like structures allows for the incorporation of additional cell support molecules (such as extracellular matrix components) to be included into the nanoparticle magnetic assemblies.

Magnetizing cells with magnetic nanoparticle assemblies consists of only adding assembly to cells in regular cell culture media. Cells can be magnetized within minutes from magnetic nanoparticle treatment (5 minutes) and either attached or suspended cells can be treated with magnetic nanoparticle assemblies. Cells can be cultured until a desired size is achieved, and then the 3D culture decellularized to produce magnetic ECM.

The 3D culture can be initiated with any cells, mixtures of cells or tissue fragments. Cell lines, heterologous or preferably autologous cells can be used. The resulting magnetic ECM prepared from the 3D cultures can then be reseeded with the desired cell types, particularly with autologous cells from a patient, such that a few cells obtained from a patient can be amplified and grown in a very natural 3D cell culture on an existing ECM matrix. The final 3D culture can then be use in cell and tissue therapies, and perhaps even in organ transplantation in the future.

For example, ECM can be prepared by 3D culture of various cell lines originating from cardiac tissue and/or various allogenic cardiac cell types, and ECM prepared by the methods of the invention. The ECM can then be seeded with a patient's own fibroblasts, endothelial cells, stem cells, progenitor cells, adult-derived inducible pluripotent stem cells and the like, and treated with the appropriate growth factors to encourage differentiation into cardiomyocytes, vascular smooth muscle, and endothelial cells, etc. The resulting tissue can be implanted and used to repair damaged heart mucle. Because the ECM is grown from more readily available cell types, yet decellularized and seeded by a variety of autologous cells, including some stem and progenitor cells, the method has the advantages of providing readily available and natural ECM that can then be a scaffold for growing rare, but safe, patient-derived cells and thus regrow a viable, safe tissue for implant use.

In our test experiments, 0.5 ml of NANOSHUTTLE™ was combined with 5 ml of human primary fibroblasts and smooth muscle cells. This mixture was gently mixed by pipette action and allowed to incubate and settle for 5 minutes. The cells were then transferred to 3.5 cm petri dish and levitated with a ring shape neodymium magnet (20× (8.5×4.5)×7 mm; pull strength: 13 lbs). All cells levitated and coalesced into a 3D culture within minutes of applying a magnetic field.

The cells were then cultured for 4 days in DMEM medium with 10% FBS. After culture, the cells were decellurized according to known techniques (see starred methods below), but using a magnet to levitate and hold the ECM, whilst washing away debri. The final ECM was stained with DAPI, which showed the ECM lacked DNA (not shown), and positively stained for collagen and laminin (not shown).

A wide variety of ECM preparation techniques that can be used with the invention are listed below:
1. Freeze at −80° C. and thaw at RT. Repeat the cycle six times. Immerse in 25 mM $NH_4OH$ aqueous solution for 20 min and wash with MilliQ water.
2. Treat with 0.1% Triton-X100 and 1.5M KCl in 50 mM Tris buffer (pH 8.0) for 6 hr. Wash with 10 mM Tris buffer (pH 8.0) and MilliQ water
3. Freeze at −80° C. and thaw at RT. Repeat the cycle 6 times. Wash with MilliQ water.
4. Immerse in 25 mM $NH_4OH$ for 1 h and wash with MilliQ water.
5. Immerse in 0.1% TX100 in 50 mM Tris buffer (pH 8.0) for 6 h. Wash with 10 mM Tris buffer (pH 8.0) and MilliQ water.
6. Incubate in 1.5M KCl for 6 h and then in MilliQ water for 6 h. Repeat three times. Wash with MilliQ water.
7. 6 cycles of freezing at −80° C. and thawing at RT. Three cycles of osmotic shock with 3M NaCl to $H_2O$. Wash with MilliQ water.
8. *5× washes with 8 mM CHAPS, 1M NaCl, and 25 mM EDTA in PBS (10 mM at pH 7.4), 10× washes with PBS, incubate overnight at 37° C. with PBS+10% FBS+10% penicillin/streptomycin; incubate tissue with benzonase (nuclease, 90 U/ml, Sigma-Aldrich) at 37° C. for 1 hour; 5× wash with PBS+10% FBS, 10% penicillin/streptomycin; store decellularized ECM at 4° C. in PBS+10% FBS, 10% penicillin/streptomycin
9. *Rinse tissue fragments 5× with PBS (10 mM pH 7.4), 5× washes in isotonic PBS+1% (w/v) Triton X-100; resuspend by gently pipetting 5×; 5× wash with isotonic PBS+2% (w/v) Triton X100; resuspend by gently pippeting 5×; rock sample overnight with isotonic PBS+3% (w/v) Triton X-100; 5× wash with isotonic PBS+3% (w/v) Triton X-100; 5 min. incubation in 2% Triton between washes; resuspend by using gently pippeting 5×; 10× wash with PBS containing 0.1% SDS (w/v); 10× wash PBS wash, Benzonase treatment as above, wash and store.
10. Freeze −80° C. 6 h; Thaw in deionized $H_2O$ 8 h; Perfuse deionized $H_2O$; then PBS 37° C. 2 h; 0.02% Trypsin 0.05% EDTA 0.05% $NaN_3$ 2 h; 4% deoxycholate 2 h; 0.1% Peracetic acid; 4% EtOH 1 h
11. 10 µM adenosine 15 min; 1% SDS 12 h; 1% Triton X-100 30 min; PBS with antibiotics 124 h
12. 8 mM CHAPS, 1 M NaCl, 25 mM EDTA 2 h; PBS with antibiotics; 90 U/ml benzonase; PBS with 10% FBS
13. 0.1% SDS 120 min; 1% Triton X-100 10 min; PBS with antibiotics 72 h
14. Freeze −80° C. 24 h; 0.02% Trypsin 2 h; 3% Triton X 18-24 h; Peracetic acid 1 h
15. Freeze −80° C.; 4° C. PBS overnight; 0.01% SDS 24 h; 0.1% SDS 24 h; 1% SDS 24 h; 1% Triton X-100 30 min; 0.1% Peracetic acid 3 h
16. Wash—PBS & freeze 1 week; Freeze/thaw 24 h; Wash—DMEM 48 h; 11% SDS 5 weeks; DNAase 24 h Seeding techniques currently employed in recellularization of ECM include injection of cells into the ECM, low dose seeding by perfusion, and multiple bolus seeding with perfusion. This can also be achieved by simply mixing cells with magnetized ECM. See FIG. 1 showing the magnetization of cells and the growth of a 3D culture, which eventually makes a magnetic ECM that can be decellularized according to known techniques. Although FIG. 1 shows a single cell type being used for 3D culture, a mixture of cell types could also be used herein.

Figure 2:
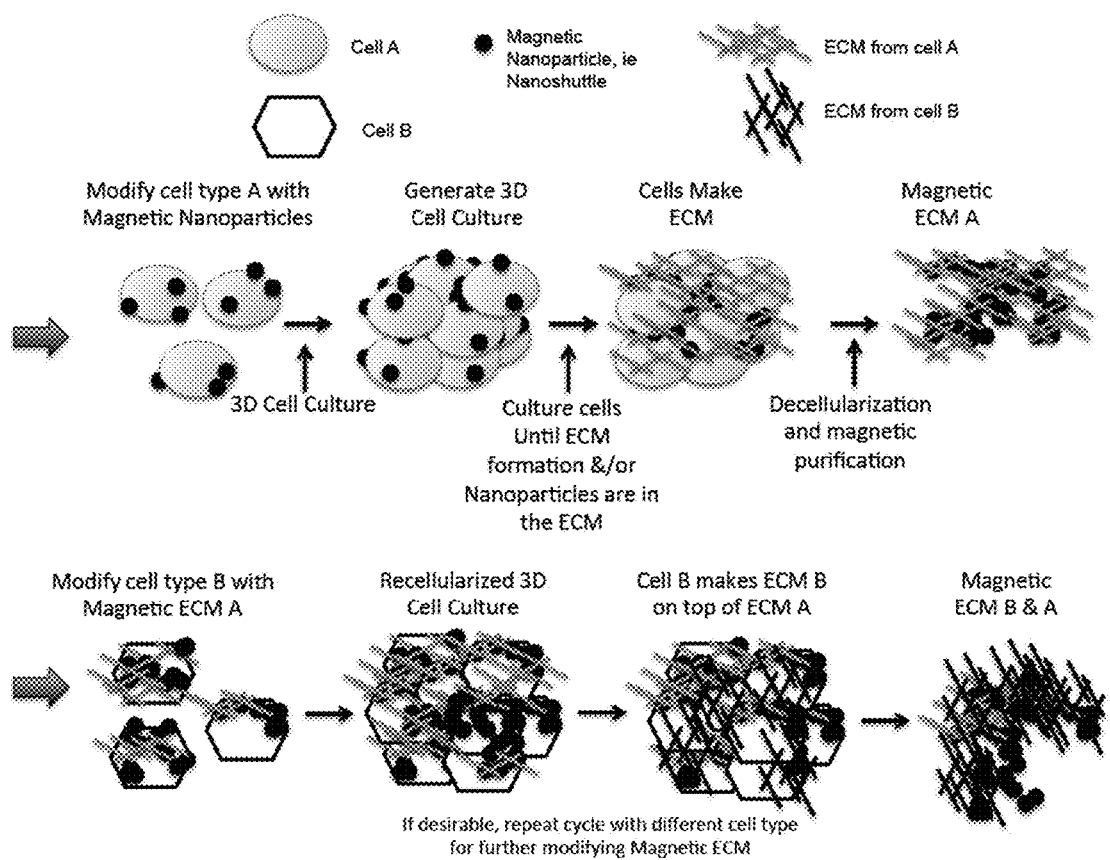
FIG. 2. Schematic of decellularization process using a two separate cell types in a sequential process, wherein Cell type A is used to make a 3D culture and thus generate ECM A, which is then used to treat Cell Type B. The final product will be magnetic ECM A further modified with ECM B. Of course, an ECM A & B mixture could also be prepared by co-culturing cells types A and in the initial 3D culture, and such method may be preferred.

The process can also be used to enrich or modify the purified magnetized ECM with cells of the same type or different type, respectively, as shown in FIG. 2. This would be achieved by recellularizing the magnetic ECM prepared as in FIG. 1 with cell type B, and then repeating the process to generate a mixed ECM made from two cell types.

A number of experiments were performed to show the usfeulness of the magnetic ECM and its value in assisting cells to grow in a more robust and natural way. One was a wound healing assay and the other a bone differentiation assay, wherein bone development was indicated by bone alkaline phosphatase level.

To make a decellularized matrix for the wound healing assay, T75 flasks of HPFs were treated with NanoShuttle™ (8 µL/$cm^2$ surface area) to incubate overnight. The next day, the HPFs were detached from their substrate and levitated in 6-well plates at a concentration of 2.8 million cells/well in 2 mL of media (DMEM, with 10% fetal bovine serum, FBS, and 1% penicillin/streptomycin, P/S) and cultured in 3D for 2 days.

Afterwards, the cultures were gradually decellularized with increasing concentrations of Triton X-100 (1%, 2%, 3%) in PBS, with an overnight incubation with 3% Triton X-100. Next, the cultures were washed with 0.1% SDS in PBS, then PBS alone, before being mechanically broken up with pipette action and incubated overnight with 90 U/mL benzoase in PBS with 1% P/S at 37° C. The next day, the decellularized cultures were washed twice with PBS and resuspended in the same volume of PBS as the total volume of NanoShuttle added to the flasks. This provide magnetic ECM from HPF cells (mECM-HPF) for use in the following assays.

We then looked at the effect of the mECM-HPF on the wound healing ability of NNDFs. T75 flasks of NNDFs were incubated with NanoShuttle™ (8 µL/$cm^2$ surface area). The next day, the cells were detached from substrate and counted. In a separate 96-well plate resting atop an array of 96 ring-shaped magnets, we added volumes of mECM-HPF in ratios between 0-2:1 with volumes corresponding to the amount of NanoShuttle™ in 200,000 cells. The mECM-HPF was allowed to pattern for 15 min at the bottom well. Next, 200,000 cells were added to each well and patterned for another 15 min. Afterwards, the magnetic field was removed, and the area of the ring was measured over 1400 minutes, then plotted against time and concentration. We found that with increasing concentrations of mECM-HPF, the ring of cells were able to close at a faster rate (Table 1). Thus, magnetic EMC from HPF cells improved the wound healing of NNDFs.

TABLE 1

Wound Healing of NNDFs

| Ratio mECM-HPF:NS | Rate of ring/wound closure |
|---|---|
| 2.00 | 1.17 |
| 1.67 | 0.82 |
| 1.33 | 1.59 |
| 1.00 | 0.75 |
| 0.67 | 0.78 |
| 0.33 | 0.58 |

Next, we studied whether the magnetic ECM from HPF helped to differentiate NNDFs into a bone phenotype. T75 flasks of NNDFs were treated with either NanoShuttle™ alone, mECM-HPF alone, or 1:1 combined NanoShuttle™: mECM-HPF (8 µL/cm² surface area) to incubate overnight. The next day, NNDFs were detached from their substrate and levitated in 24-well plates at a concentration of 200,000 cells/well in 400 µL of media. The NNDFs were further split between cultures with DMEM media, and cultures with osteogenic media (DMEM with 10% FBS, 1% P/S, 10 mM β-glycerolphopshate, 100 nM dexamethasone, 50 µg/mL ascorbic acid).

Concomitantly, NNDFs treated with NanoShuttle™, and untreated NNDFs were plated in 2D with either media types. The cultures were cultured for 6 days, with media changes every 2 days. After 6 days, the 3D cultures were homogenized in 2% Triton X-100 in PBS, then centrifuged for 15 min at 10,000 g at 4° C. 2D cultures were similarly washed in 2% Triton X-100 in PBS, then centrifuged for 10 min at 2,500 g at 4° C. The supernatants were collected and analyzed using an bone alkaline phosphatase assay kit (SensoLyte®).

Bone alkaline phosphatase (BAP) is the bone-specific isoform of alkaline phosphatase, and the change of alkaline phosphatase activity is involved in a variety of physiological and pathological events, such as bone development, bone-related diseases, gestation-related diseases and inflammatory bowel diseases. Alkaline phosphatase is also a popular enzyme conjugated with secondary antibody for ELISA. p-Nitrophenyl phosphate (pNPP) is proven to be an effective chromogenic substrate for alkaline phosphate.

Samples of the supernatants were aliquotted and the alkaline phosphatase substrate, pNPP, was added at a 1:1 concentration. The solutions were mixed and the absorbances of the samples were then read on a spectrophotometer at an absorbance of 405 nm.

The results are shown in Table 2, and confirm that the addition of mECM-HPF to 3D cultures with osteogenic media increased BAP activity over those 3D cultures with no decellularized matrix, or a 1:1 ratio of NanoShuttle: mECM-HPF and osteogenic media. Thus, the addition of mECM-HPF increased bone development and improved the differentiation of NNDFs towards a bone phenotype in 3D culture.

TABLE 2

BAP Activity (relative to 2D untreated control without osteogenic media)

| | | Osteogenic Media | |
|---|---|---|---|
| | | − | + |
| 3D | +mECM-HPF | 0.265 | 0.402 |
| | +NS/mECM-HPF | 0.239 | 0.315 |
| | +NS | 0.222 | 0.274 |
| 2D | +NS | 0.805 | 1.511 |
| | untreated | 1 | 1.229 |

In future test experiments, we will characterise and evaluate the performance of the magnetic ECM versus cells cultured with Nanoshuttle only. We will assess the efficacy of cells grown in our magnetic ECM against cells treated with Nanoshuttle. This experiment will include determining the yield of levitating cells versus non-levitated when treated with Magnetic ECM vs. Nanoshuttle. Next, we will evaluate the level of inflamatory cytokines, IL-6 and IL-8, in the supernatant of treated and levitated cultures versus the control system consisting of monolayer cultures and cells treated and levitated with Nanoshuttle only.

We will also investigate the effect of time of levitation on the composition of the magnetic ECM by probing ECM proteins with immunohistochemisty and/or western blotting. We will also characterize the magnetic ECM generated from a single cell type, more than one cell type levitated and co-cultured at the same time, and two cell types where one cell type generates the first batch of magnetic ECM (magnetic ECM A) that is then used to treat a second cell type (magnetic ECM B) which is levitated to further modify the original magnetic ECM (FIG. 2).

Finally, we will assess whether the magnetic ECM has any effect on regulating differentiation of pre-adipocyte stem cells (3T3 fibroblasts) into adipocytes versus cells treated/levitated with nanoshuttle only and in 2D. This will be accomplished by inducing differentiation into adipocytes of levitated cells (magnetic ECM and NANOSHUTTLE™ treated) and monolayers (magnetic ECM and NANOSHUTTLE™ treated and non-treated). We anticipate that our magnetic ECM will provide an easily obtainable and hospitable environment for the growth and correct differentiation of stem cells to make various tissue types.

The following reference are incorporated herein in their entirety for any and all purposes.

Lu H., et al., Comparison of decellularization techniques for preparation of extracellular matrix scaffolds derived from three-dimensional cell culture, J Biomed. Mater. Res. 00A:000-000 (2012) (article preview available online).

Reilly, G. C. & Engler, A. J., Intrinsic extracellular matrix properties regulate stem cell differentiation, J. Biomech. 43(1): 55-62 (2010).

WO2010036957 & WO2011038370
WO2006060171

What is claimed is:
1. A magnetic extracellular matrix (ECM) made by:
 a) placing magnetic nanoparticles inside a cell;
 b) levitating said cell in a magnetic field and growing said levitated cell in said magnetic field into a 3D culture of cells having an ECM until said magnetic nanoparticles are lost from said cells and retained by the ECM; and
 c) decellularizing said 3D culture of cells using a magnet to levitate and hold said ECM while washing away cell debris to produce a magnetic ECM.

2. The magnetic ECM of claim 1, wherein said magnetic nanoparticles further comprise:
   i) a negatively charged nanoparticle;
   ii) a positively charged nanoparticle; and
   iii) a support molecule;
   wherein one of said negatively charged nanoparticle or positively charged nanoparticle contains a magnetically responsive element, and wherein said support molecule holds said negatively charged nanoparticle and said positively charged nanoparticle in an intimate mat-like admixture.

3. The magnetic ECM of claim 1, wherein decellularizing step consists essentially of one or more of freeze-thaw, detergent, or osmotic pressure treatments applied to said 3D culture of cells.

4. The magnetic ECM of claim 2, wherein decellularizing step consists essentially of one or more of freeze-thaw, detergent, or osmotic pressure treatments applied to said 3D culture of cells.

5. A magnetic extracellular matrix (ECM) made by:
   a) placing magnetic nanoparticles inside a cell;
   b) levitating said cell in a magnetic field and growing said levitated cell in said magnetic field into a 3D culture of cells having an ECM until said magnetic nanoparticles are lost from said cells and retained by the ECM; and
   c) decellularizing said 3D culture of cells using a magnet to levitate and hold said ECM while washing away cell debris to produce a magnetic ECM, wherein said decellularizing consists essentially of one or more of freeze-thaw, detergent, or osmotic pressure treatments applied to said 3D culture of cells.

6. A method of preparing tissue for implantation in a patient, said method comprising:
   a) seeding the magnetic ECM of claim 1 with allogeneic stem or progenitor cells from a patient;
   b) growing said seeded ECM in a magnetic field; and
   c) transplanting the seeded ECM from step b) into said patient.

7. The method according to claim 6, wherein in step a) the magnetic ECM is further seeded with fibroblast cells, epithelial cells, osteoblast cells, or autologous fibroblast cells and epithelial cells.

8. A method of preparing a seeded magnetic ECM, said method comprising:
   a) seeding the magnetic ECM of claim 1 with allogeneic stem or progenitor cells from a patient;
   b) growing said seeded ECM in a magnetic field.

9. The method according to claim 8, wherein in step a) the magnetic ECM is further seeded with fibroblast cells, epithelial cells, osteoblast cells or autologous fibroblast cells and epithelial cells.

10. A seeded magnetic ECM made by the method of claim 8.

* * * * *